United States Patent [19]
Wiesent et al.

[11] Patent Number: 5,377,249
[45] Date of Patent: Dec. 27, 1994

[54] COMPUTER TOMOGRAPHY APPARATUS HAVING A PARTIAL RING X-RAY SOURCE AND A PARTIAL RING DETECTOR

[75] Inventors: Karl Wiesent; Ernstpeter Ruehrnschopf; Johannes Ebersberger, all of Erlangen, Germany

[73] Assignee: Siemens Aktiengesellschaft, Munich, Germany

[21] Appl. No.: 980,974

[22] Filed: Nov. 24, 1992

[30] Foreign Application Priority Data

Nov. 28, 1991 [DE] Germany .................. 4139150

[51] Int. Cl.⁵ .......................................... G01N 23/083
[52] U.S. Cl. ............................................ 378/4; 378/10; 378/901; 364/413.17
[58] Field of Search ............... 364/413.15, 413.16, 364/413.17; 378/4, 8, 10, 12, 14, 19, 901

[56] References Cited

U.S. PATENT DOCUMENTS

| | | | |
|---|---|---|---|
| 2,319,350 | 5/1943 | Schiebold | 378/71 |
| 4,075,489 | 2/1978 | Neal et al. | 378/10 |
| 4,122,346 | 10/1978 | Enge | 250/398 |
| 4,129,783 | 12/1978 | Houston | 250/445 T |
| 4,130,759 | 10/1978 | Haimson | 378/10 |
| 4,135,095 | 1/1979 | Watanabe | 378/9 |
| 4,158,142 | 6/1979 | Haimson | 378/10 |
| 4,352,021 | 9/1982 | Boyd et al. | 378/12 |
| 4,590,558 | 5/1986 | Glover et al. | 364/413.19 |
| 4,845,626 | 7/1989 | Ohhashi | 364/413.16 |
| 4,914,681 | 4/1990 | Klingenbech et al. | 378/12 |
| 4,962,513 | 10/1990 | Schwierz et al. | 378/12 |
| 5,191,600 | 3/1993 | Vincent et al. | 378/10 |

FOREIGN PATENT DOCUMENTS 0127983 12/1984 European Pat. Off. .

OTHER PUBLICATIONS

"Optimal Short Scan Convolution Reconstruction for Fanbeam CT," Parker, Med. Phys. 9(2), Mar./Apr. 1982, pp. 254–257.

*Primary Examiner*—Paul M. Dzierzynski
*Assistant Examiner*—David V. Bruce
*Attorney, Agent, or Firm*—Hill, Steadman & Simpson

[57] ABSTRACT

A computer tomography apparatus has an anode in the form of a partial ring along which a focus is electronically moved to generate a scan beam from different directions, and a partial ring detector which generates a number of data sets from the attenuated radiation at the different directions, includes a computer wherein the data sets are weighted independently of the measured values so that image reconstruction can be undertaken with a standard computer tomography method, such as convolution and back-projection. The weighting is selected so that the boundaries of regions having constant values represent smooth curves in the sinogram. The image can thereby be reconstructed without complementary interpolation, which is normally required in computer tomography systems having a partial ring x-ray source and detector.

4 Claims, 9 Drawing Sheets

COMPUTER TOMOGRAPHY APPARATUS HAVING A PARTIAL RING X-RAY SOURCE AND A PARTIAL RING DETECTOR

BACKGROUND OF THE INVENTION

1. Field of the Invention

The present invention is directed to a computer tomography apparatus of the type having a partial ring x-ray source, over which a focus is electronically moved to generate an x-ray beam for transilluminating a measurement field from different directions, and a partial ring detector in the form of a row of detector elements which, in combination, generate a plurality of data sets from the respective directions, from which an image can be reconstructed in a computer.

2. Description of the Prior Art

In conventional computer tomography systems employing a partial ring x-ray source (radius $R_F$ and arc $R_F$) and a partial ring detector (radius $R_D$ and arc $R_D$), the sinogram, i.e., the arrangement of the detector data sets in a matrix, is only partially filled.

In order to obtain a complete image, therefore, some type of interpolation is necessary.

This problem is caused by the use of the partial rings, and is independent of the specific manner by which the focal spot is generated (for example, deflected electron beam, surface heating with a deflected laser beam, or revolving tube), is independent of the type of measurement (for example, using individual detectors), and is independent of geometrical factors with respect to the z-direction such as, for example, both partial rings being disposed in the same plane (which can be achieved by nutation of the detector partial ring), the partial rings being offset in z-direction, continuous advancing of the patient support during the measurement (spiral CT), and various combinations of these factors.

For explaining the problem, FIG. 1 shows an exemplary apparatus having an anode and a detector ring which are offset in the z-direction, and a patient support which is displaceable (advanceable) during the exposure. Further details of the operation of this type of system are described below.

The manner by which partial fan beams of variable size arise as result of the partial rings, in addition to full fan beams, i.e., fan beams which entirely cover the examination region, is shown in FIGS. 2 and 3. The measured values are usually characterized by two angle variables, with alpha being the angular position of the fan beam center (which is also the center of the detector ring), and beta being the angular position within the fan beam. The matrix of the data compiled in an alpha-beta coordinate system is referred to as the sinogram, with an exemplary sinogram being shown in FIG. 3. In the exemplary apparatus of FIG. 2, the detector is referenced 7, the anode is referenced 3, and the measurement field is referenced 6.

Measured values which correspond to a transillumination of the subject in identical paths (straight lines), but in an opposite propagation direction, are referred to as complementary. FIGS. 4 through 7 respectively illustrate the definition of the measured values and their classification as shown in FIG. 3. In FIG. 3, the region designated (0) indicates that data for those alpha-beta coordinate values are lacking, i.e., either a detector section or a focal path section corresponding to those angles is not present. The region of the matrix designated (1) means that single data points are present, i.e., a detection value is present but a complementary value is lacking. The regions designated (2) and (2*) indicate double values are present, i.e., data point and it complementary value are both present, respectively contained in the regions (2) and (2*).

The device geometry is referred to as "minimal" when at least one measured value is present for every point of the examination region (the central circle in FIG. 2) and for every direction. In systems having rings of smaller circumferential extent, this property may not be present.

The angles for measuring a ray AB (used as an example) are schematically shown in FIG. 4. The angles for measuring the complementary ray A'B' are schematically shown in FIG. 5. The conditions for a minimal geometry are schematically indicated in FIG. 6 where $R_o$ designates radius of measurement field. FIG. 7 shows the manner by which the respective rays are classified, consistent with the sinogram occupation designations shown in FIG. 3, for the minimal partial ring geometry of FIG. 2.

A technique for image reconstruction on the basis of weighting of the data of the complementary areas (2) and (2*) of a sinogram obtained in a CT apparatus of the fourth generation, having a full 360° anode ring and a minimal detector ring, is described in the article "Optimal Short Scan convolution Reconstructions for Fan-beam CT," Parker, Med. Phys. 9(2), March/April 1982, pp. 254–257.

If both rings are only partial rings, the usual image construction technique requires that "artificial" measured data be created by interpolation into the complementary data, in order to convert the sinogram into the type which can be used in the so-called "Parker weighting" exemplified by the above article, wherein a hypothetical, complete anode ring is postulated.

Such complementary interpolation has the following disadvantages. First, data inconsistency exists. This is because for physical and technical reasons, the measured values from the opposite directions do not precisely coincide, since the fan beams from the opposite directions cannot be precisely the same. The inconsistency of neighboring measured values within a fan beam is further intensified by the convolution, and easily results in artifacts in the image. This disadvantage is generally attempted to be countered by undertaking a mathematical data smoothing, however, any such smoothing results in some information loss. A second disadvantage is that, except in the case of very specific angle relationships, an interpolation is always necessary, which can generate additional artifacts. A third disadvantage is that in systems of the type wherein the anode and detector rings are offset in z-direction, and/or wherein the patient support is advanced during the measurement, the inconsistency of the data is drastically intensified. A fourth disadvantage is the complex and expensive hardware outlay which is necessary. Such hardware is necessary because the processing of individual fan beams independently of each other, which is standard in conventional pre-processing and convolution (such as according to the pipeline principle in which data can be processed in parallel) is interrupted, because input data from different fan beams are required for augmenting a data set with the artificially created values.

SUMMARY OF THE INVENTION

It is an object of the present invention to provide a computer tomography apparatus, and a method for operating such an apparatus, of the type having partial anode and detector rings such that a sinogram is generated which contains the aforementioned lacking (=(0)), single (=(1)) and double (=(2) and (2*)) data regions, which still permits standard CT reconstruction techniques to be used in a standard CT image reconstruction unit, while avoiding the data discontinuities or aberrations which are normally present in double partial ring systems.

This object is achieved in a method and apparatus wherein the boundary lines (curves) between the aforementioned regions in the sinogram are identified and are modified in a manner which smooths the sharp corner or "kink" which is characteristic of double partial ring systems. Weighting functions are then formulated for the measured values represented by the modified curves, and the data can then be weighted in a preprocessing unit. The data can then be forwarded for processing in a standard CT image reconstruction unit as though each fan beam had a complete set of measured values associated therewith. As used herein a "standard CT image reconstruction unit" and "standard CT image reconstruction techniques" refer to those known techniques, typically convolution and back-projection, which operate on a full data matrix.

The method and apparatus disclosed herein have the following advantages. The advantages of a double partial ring design are preserved, such as the cost and equipment savings in only having to construct partial, as opposed to complete, anode and detector rings. The aforementioned hardware for complementary interpolation is avoided. The calculating speed is comparable to that achieved in conventional CT systems, because the pipeline principle and the possibility of parallel data processing of data from individual fan beams can be implemented. The aforementioned disadvantages which diminish the image quality (data inconsistency, interpolation errors, etc.) associated with complementary interpolation are avoided. Moreover, in all CT systems, including that disclosed herein, the z-geometry (with or without ring offset, with or without patient advancement) influences the back-projection algorithm. In the method and apparatus disclosed herein, the handling of the data comprising each data set in the pre-processing, for resolving problems arising due to the use of double partial rings, can ensue in the same manner in all versions of z-direction geometry, because the inventive method is independent of the back-projection algorithm which is employed.

DESCRIPTION OF THE PREFERRED EMBODIMENTS

Figure 1:
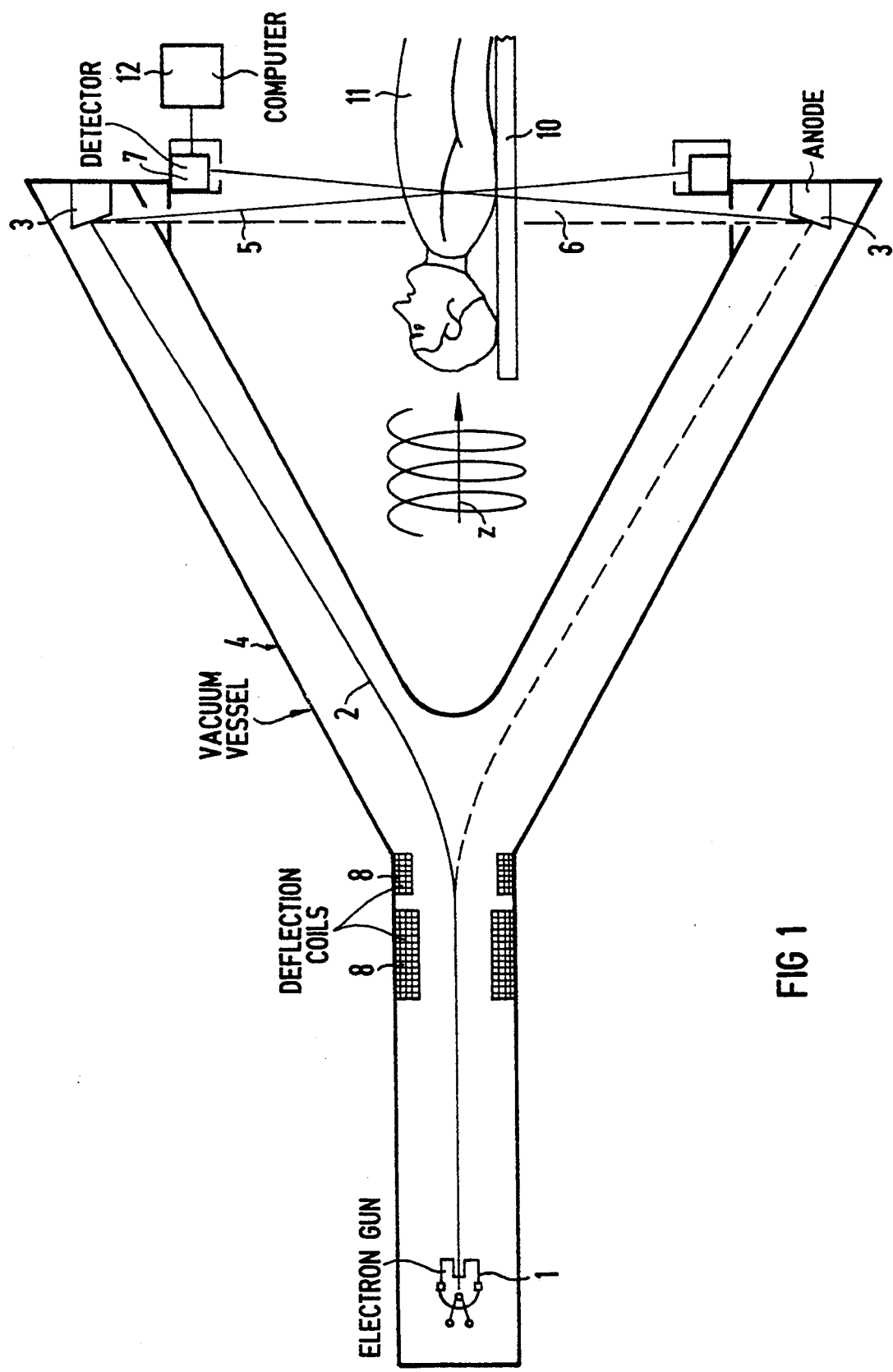
FIG. 1 is a side view of a double partial ring computer tomography apparatus, constructed in accordance with the principles of the present invention.

As noted above, a computer tomography apparatus is shown in FIG. 1 having an electron gun 1 which emits an electron beam 2 which is incident on an anode 3. The anode 3 is in the form of a partial ring. The electron beam 2 proceeds through a vacuum vessel 4 formed by various connected sections, with the anode 3 being disposed at one end of the vacuum vessel 4. The electron beam 2 is deflected on the anode 3 by means of deflecting coils 8 so that a focus travels over the anode 3 along a path approximating a segment of a circle. A fan-shaped x-ray beam 5 emanates from this moving focus. For transillumination of a measurement field 6 from different directions, the x-ray beam 5 moves (rotates) around the system axis by appropriate focus motion on the anode 3. After emerging from the measurement field 6, the attenuated x-ray beam 5 is incident on a detector 7, which is also in the form of a partial ring. The detector 7 consists of a row of individual detector elements, each of which generates an electrical signal corresponding to the radiation incident thereon. The signals from a group of the detector elements corresponding to a fan beam from a given direction constitute a data set for that direction. As usual for fourth generation scanners (inverse geometry) the data collected by a single detector element are used as a mathematical fan for reconstruction.

The fan plane of the x-ray beam 5 proceeds perpendicular to the plane of the drawing. The detector 7 is slightly offset in the z-direction relative to the anode 3, so that the x-ray beam 5 proceeds obliquely through a patient 11 until it arrives at the detector 7 at the opposite side. The vacuum in the vacuum vessel 4 and in the electron gun 1 is maintained by pumps (not shown). A support 10 on which the patient 11 lies can also be introduced into the measuring field 6. The support 10 can be advanced along the z-direction during the measurement, to conduct a scan of the type known as spiral CT. A computer 12 reconstructs by calculation an image of the patient 11 from the measured values from the detector elements of the detector 7.

Figure 8:
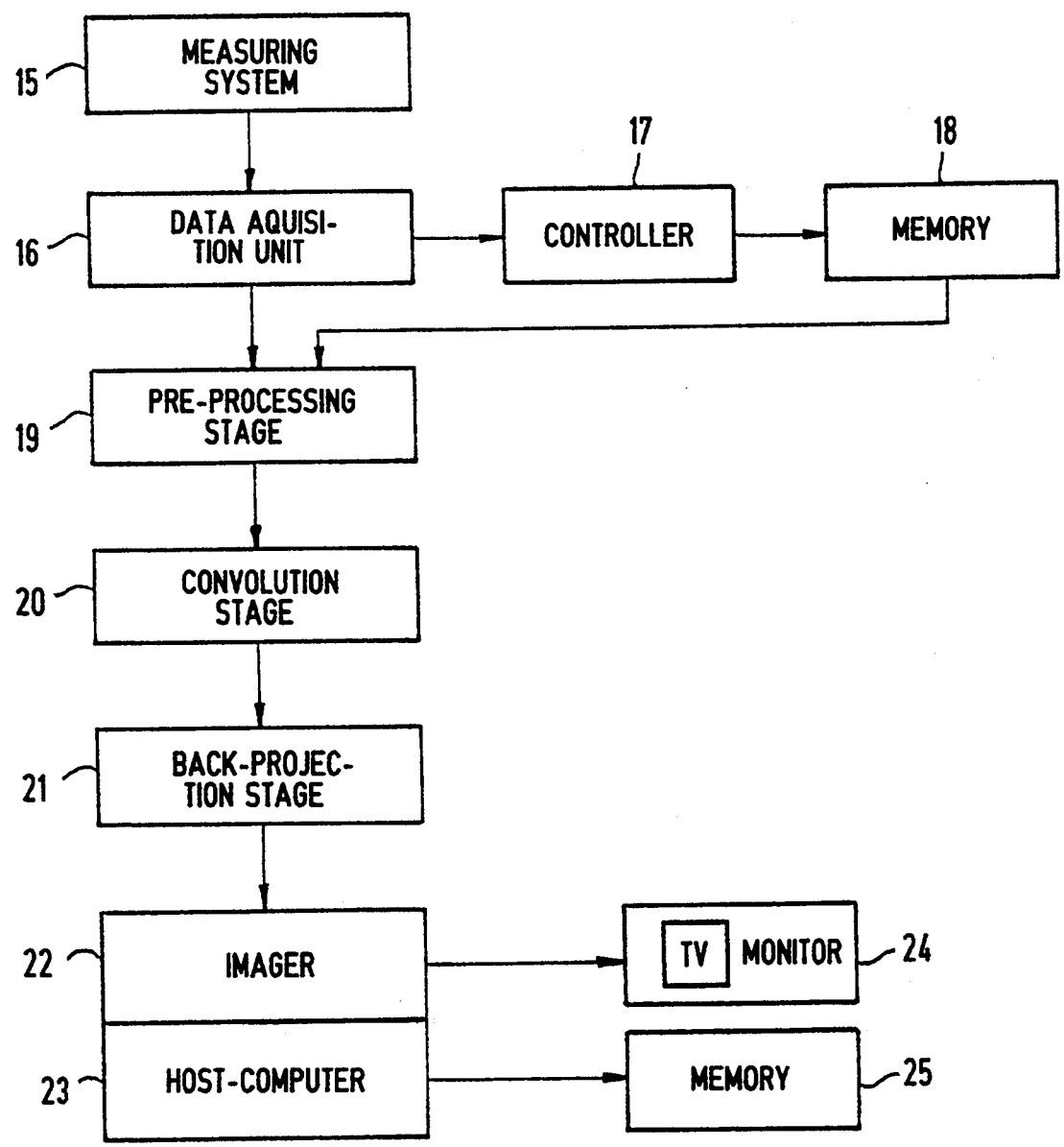
FIG. 8 is a schematic block diagram of the image reconstruction components of a computer tomography apparatus constructed in accordance with the principles of the present invention.

The basic function elements of a computer tomography system operating in accordance with the principles of the present invention are shown in FIG. 8. The functioning of the computer tomography apparatus in accordance with the invention is generally the same as in known systems insofar as transfer of data from one functional block to the next, however, as discussed in detail below, the pre-processing of data which takes place in the pre-processing stage 19 in accordance with the principles of the present invention permits standard convolution and back-projection to be undertaken in the convolution stage 20 and the back-projection stage 21, which is normally not possible in conventional partial double ring systems.

In FIG. 8, the measurement system, encompassing the structure shown in FIG. 1, is schematically indicated as block 15. The electrical signals from the individual detector elements are transferred from the measurement system 15 to the remaining processing units through a data acquisition stage 16. Some or all of the data may be transferred through a controller 17 to a memory 18 for signal editing or other purposes. The data is supplied either from the data acquisition stage 16 or from the memory 18 to a pre-processing stage 19, in which different weightings are given to the data, as described in detail below. The weighted data emerging from the pre-processing stage 19 are then supplied to standard convolution and back-projection stages 20 and 21. The output of the back-projection stage 21 is supplied to an imager 22, in which an image from the data is reconstructed under the control of a host-computer 23, and video signals corresponding to that image are supplied to a television monitor 24. The host-computer 23 has a memory 25 associated therewith for use in the image reconstruction. All of the components shown in FIG. 8, with the exception of the measuring system 15 and the television monitor 24, are encompassed within the generally-designated computer 12 in FIG. 1.

Different weightings of the measured values (calibration, standardization, cos-weighting matched to the particular back-projection algorithm employed, etc.) are undertaken in the pre-processing stage 19. The weighting data are taken from loadable tables. The weighting conditioned by the partial ring, in accordance with the principles of the present invention, can be most easily implemented by multiplication by a weighting factor with other weighting tables, independently of measured values.

Figure 2:
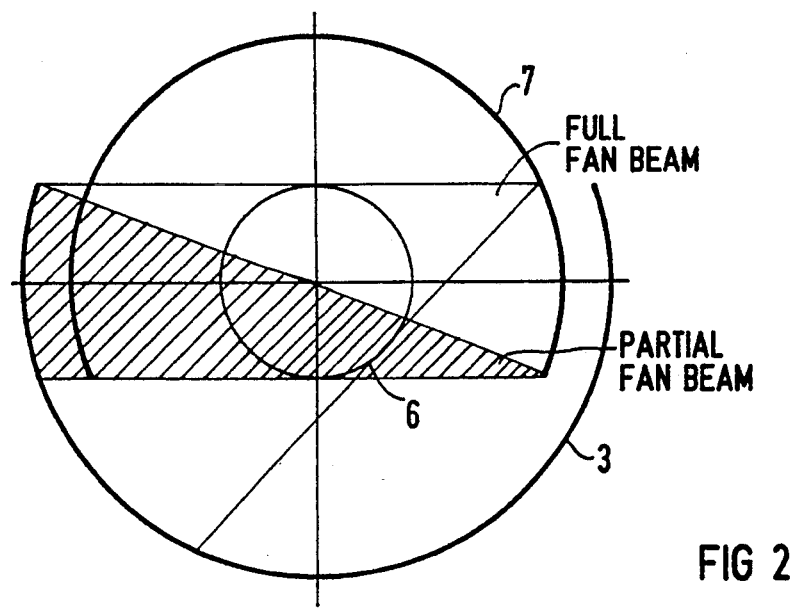
FIG. 2 is a schematic longitudinal elevation of the computer tomography apparatus of FIG. 1, showing the relationship of the fan beams to the examination area.
Figure 9:
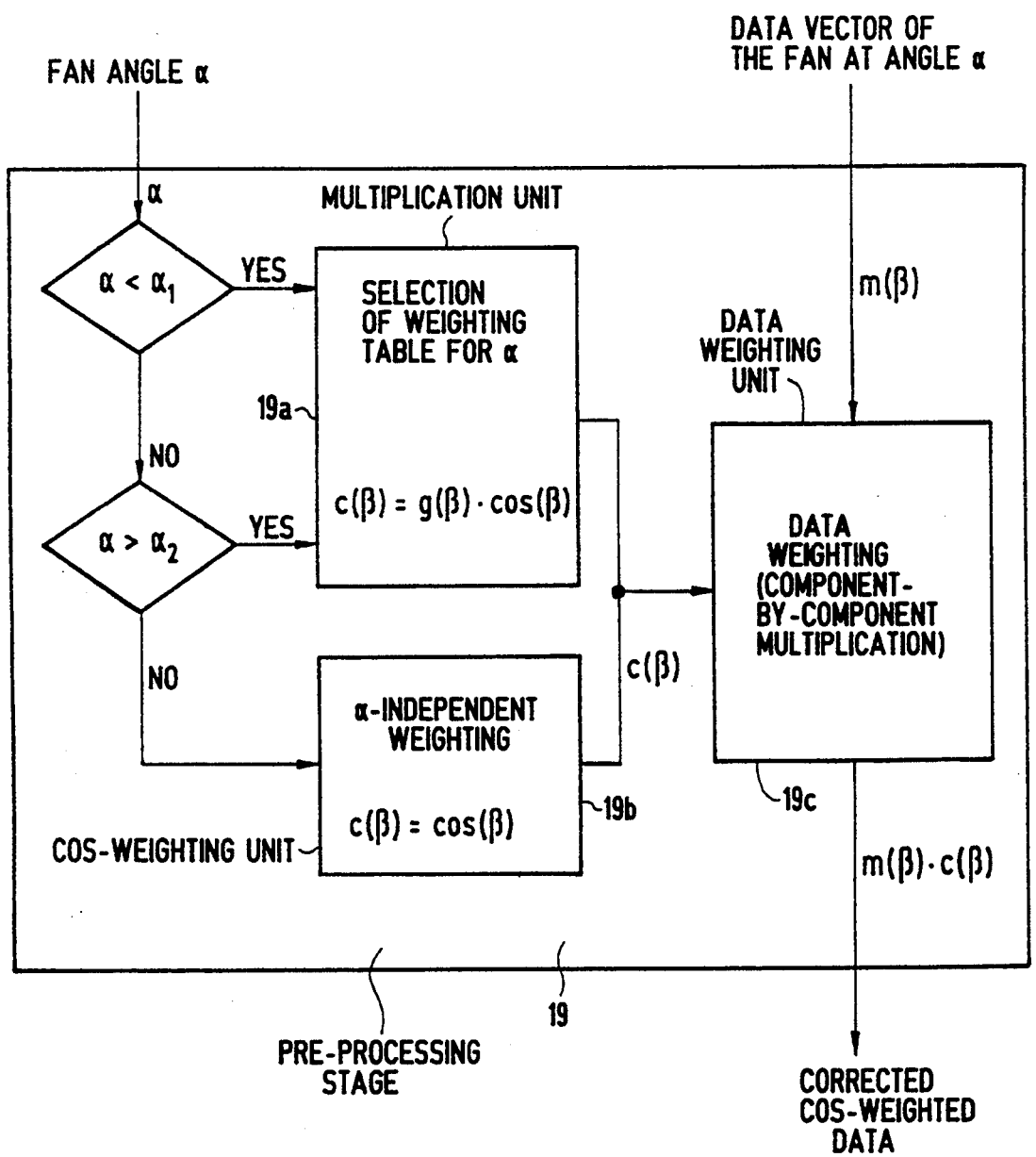
FIG. 9 is a flow chart illustrating an example of cos-weighting in a method in accordance with the principles of the present invention.

An exemplary sequence using the example of cos-weighting is shown in FIG. 9. Instead of an alpha-independent cos-table, a plurality of tables are stored. A table c ($\beta$) for weighting the data of the fan beam belonging to the angle $\alpha$ is selected dependent on the angle $\alpha$, and is made available to a multiplication unit 19a. If the angle $\alpha$ does not lie between $\alpha_1$ and $\alpha_2$ (which limit those regions for which all values corresponding to a fixed x are measured exactly once, as discussed in connection with FIGS. 2 and 3), the cos-weighting factor is multiplied by a further weighting factor g ($\beta$), obtained as described below. Otherwise, the normal cos-weighting factor is used in the conventional manner, in a cos-weighting unit 19b. The outputs of the multiplication unit 19a and the cos-weighting unit 19b are combined and supplied to a data weighting unit 19c which operates on the incoming measured values m ($\beta$) to provide output data which has been cos-weighted, and partially corrected (as needed) in accordance with the invention.

Because of the initial inquiry which is made to determine whether the angle in question is between $\alpha_1$ and $\alpha_2$, only one multiplication unit 19a is needed. It is possible, however, to sore a separate table for every angle $\alpha$, in which case the incoming signal will automatically be multiplied appropriately, as needed, and the initial decisional inquiry can be omitted.

It is also possible to implement the partial ring weighting in accordance with the invention in a separate calculating unit. Combining the various weightings in a separated, initialization step, however, yields the greatest advantages with respect to calculating time and hardware outlay, if image reconstruction is to be undertaken according to the pipeline principle, with image reconstruction taking place in parallel with the measurement.

The section of the weightings for the partial ring correction is important to the method and apparatus disclosed herein. A suitable determination is set forth below with reference to an example. Except for a global constant, the weightings g ($\alpha$, $\beta$) are defined in the following way ob observation of the sinogram of the type shown in FIG. 3:

g ($\alpha,\beta$)=0 for ($\alpha,\beta$) from region (0), g ($\alpha,\beta$)=1 for ($\alpha,\beta$) from region (1) and g ($\alpha^*,\beta^*$)=1−g ($\alpha,\beta$) when ($\alpha,\beta$) and ($\alpha^*,\beta^*$) are complementary to one another (regions (2) and (2*)).

Figure 3:
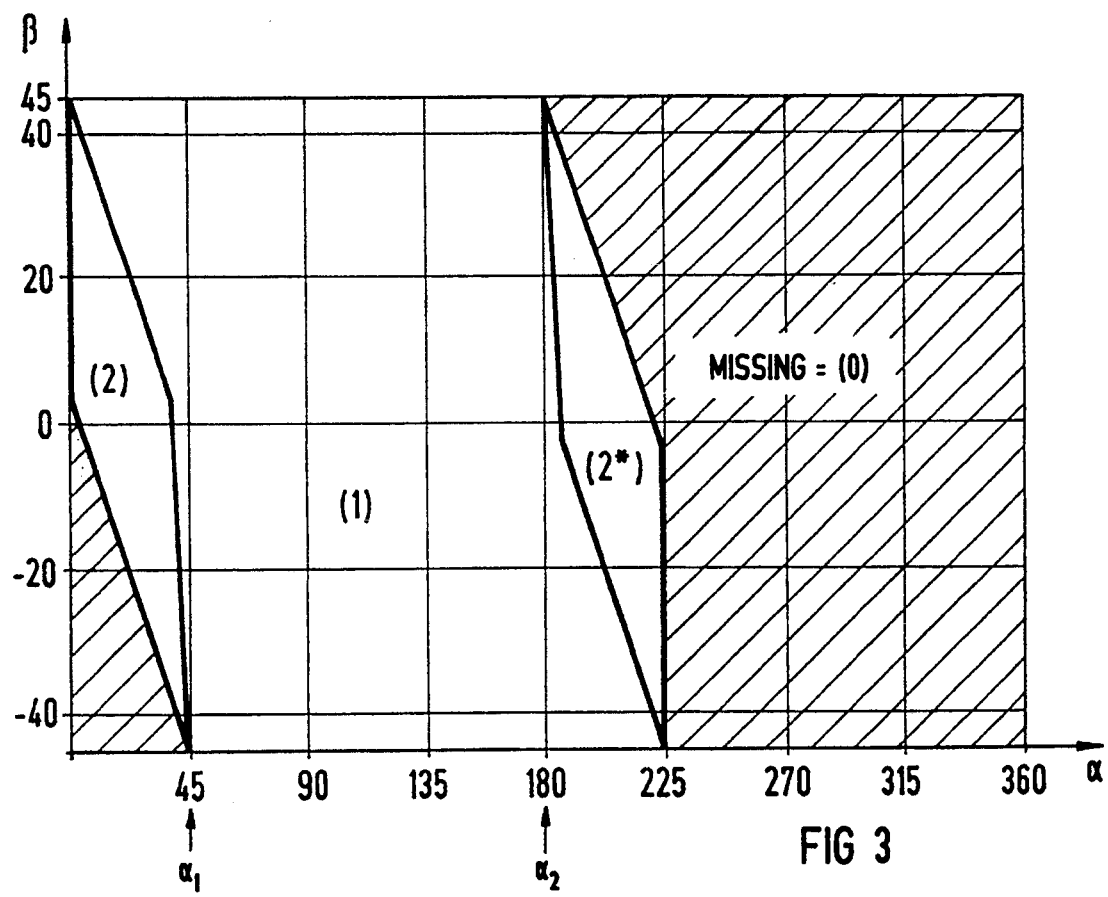
FIG. 3 is an example of a sinogram obtained in a conventional double partial ring computer tomography apparatus.
Figure 4:
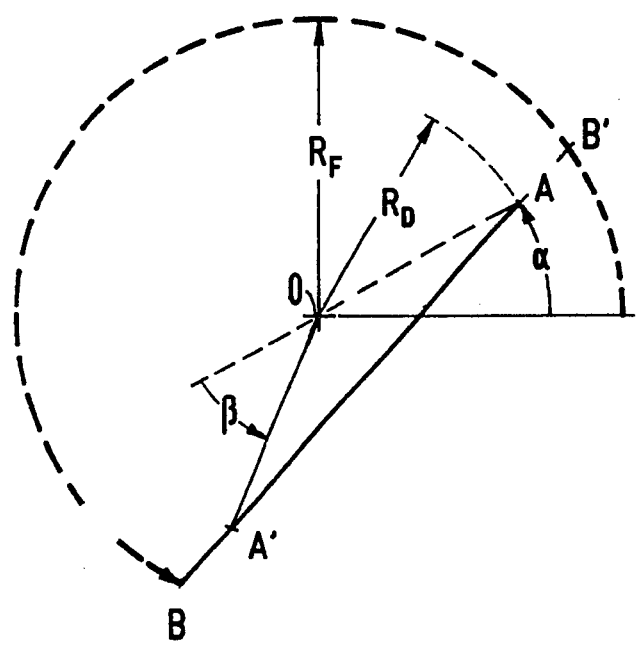
FIGS. 4, 5, 6 and 7 respectively illustrate the definition of the measured values and their classification into the regions designated in the sinogram of FIG. 3.
Figure 5:
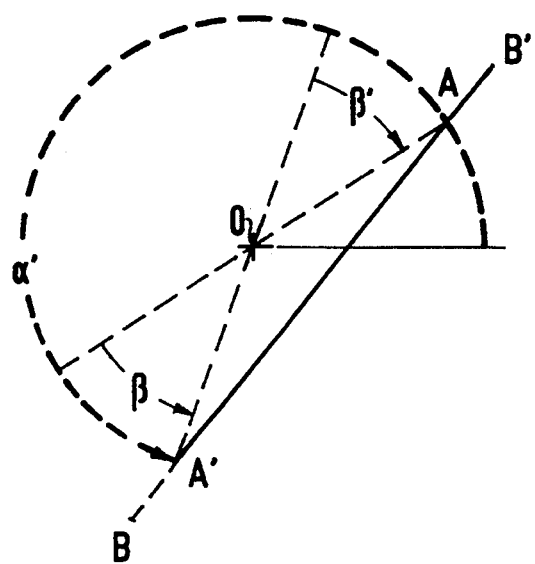
Figure 6:
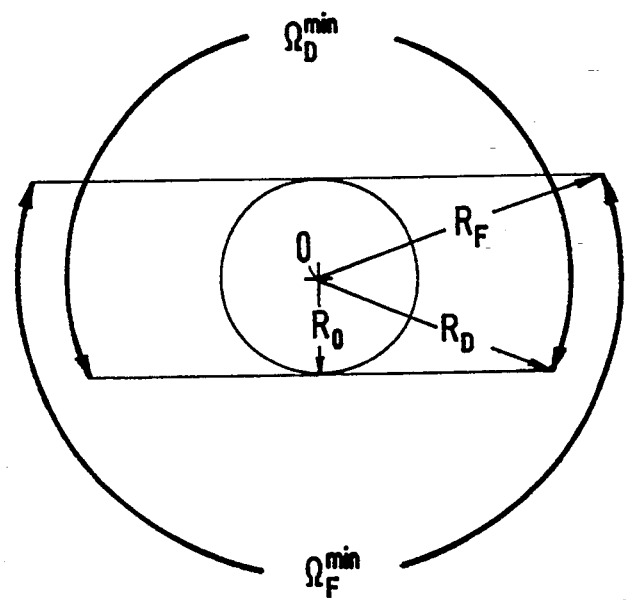
Figure 7:
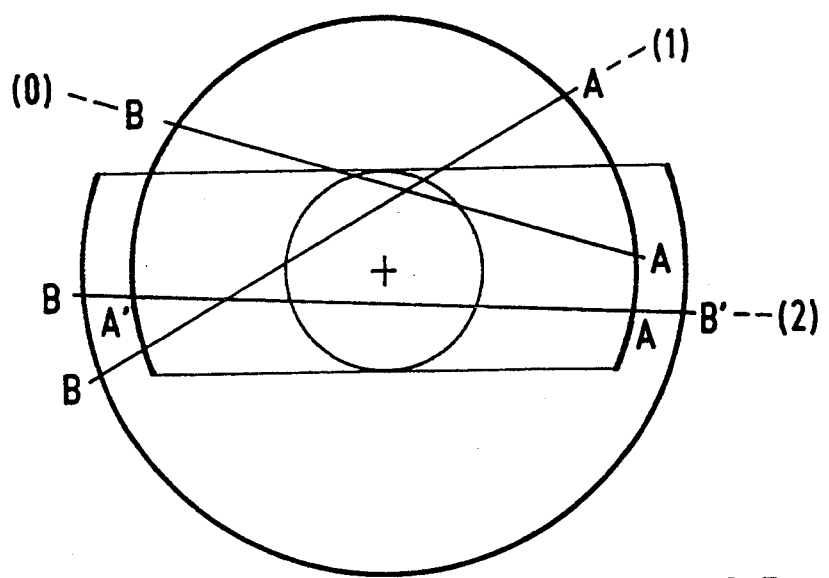

Since the first two cases are straightforward, it is sufficient below to discuss further only the weighting which takes place for measured values from the regions (2) and (2*) from FIG. 3. The goal is that the weighting function undergoes a smooth decreases in the transition from region (1) to region (0). Mathematically idealized, g ($\alpha,\beta$) should be differentiatable everywhere with respect to $\alpha$ and $\beta$.

Figure 10:
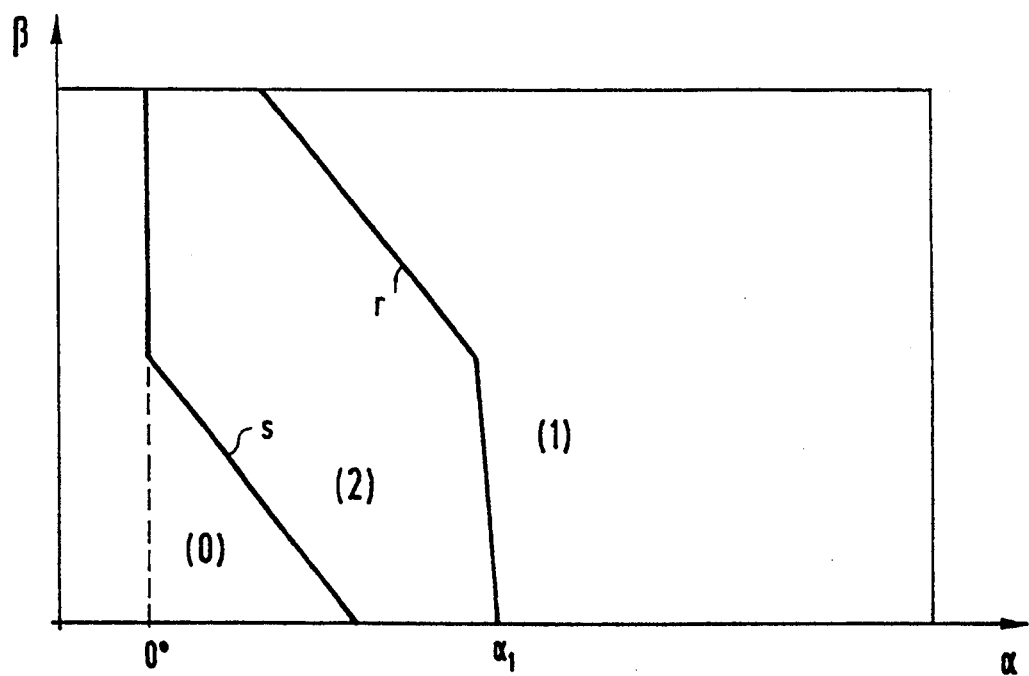
FIG. 10 is a magnified part of a sinogram as is initially obtained in the computer tomography apparatus of the invention.
Figure 11:
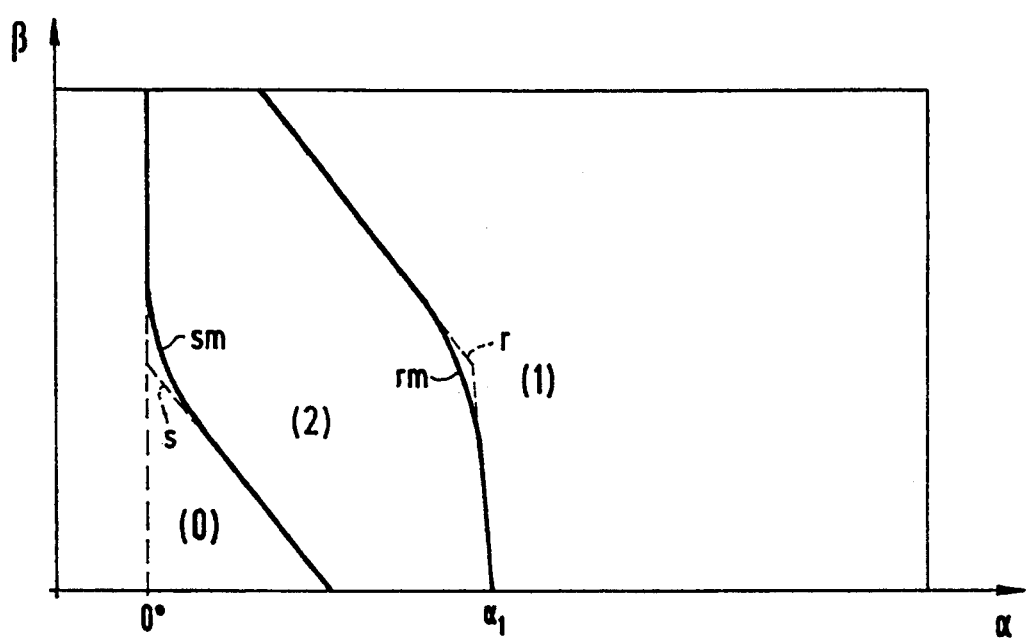
FIG. 11 is a modified sinogram version of FIG. 10 obtained in accordance with the principles of the present invention.

A suitable procedure is to first formulate (identify) the boundary curves of the sinogram regions. In this example, $\alpha$=r($\beta$) describes the boundary between the regions (1) and (2), and $\alpha$=s($\beta$)describes the boundary between the regions (2) and (0), i.e., the left edge in FIG. 3. These curves are then modified to eliminate the "kink" or sharp corner which each curve exhibits, as shown in the simplified representation of FIG. 10. These sharp corners are eliminated by modification using, for example, a cubic spline function. This smooths the curves so as to result in respective modified curves rm and sm, without the sharp corners, as shown in the simplified representation in FIG. 11. The previously-existing sharp corners of the curves r and s are also shown in FIG. 11 in dashed lines. Data in the region between the curves r and rm are weighted with 1, and data between curves s and sm are weighted with 0, i.e., g ($\alpha$, $\beta$)=1 for rm ($\beta$)<$\alpha$<r ($\beta$), and g ($\alpha$, $\beta$)=0 for s ($\beta$)<$\alpha$<sm ($\beta$).

in the remaining region for which weighting has not as yet been defined, a function x ($\alpha$, $\beta$) is defined as follows:

x ($\alpha,\beta$)=($\alpha$−sm ($\beta$))/(rm ($\beta$)−sm ($\beta$)).

g($\alpha$, $\beta$)=G(x), wherein the function G is a suitable, smooth function of x, for example, G(x)=sin$^2$ ($\pi^*$x/2).

The smoothness of the boundary curves is important in the inventive method and apparatus for achieving good results. The modification of the sharp-cornered curves disclosed herein physically corresponds to eliminating the use of a few measured values, since for example those measured values falling within the region between the curves s and sm, are weighted with zero. A theoretical alternative is to modify the data acquisition unit 16 in terms of hardware, so that the measured values corresponding to the aforementioned zero-weighted regions of FIG. 11 are not acquired at all, or are discarded. The smooth curves rm and sm would thus arise as the boundary curves in the sinogram from the beginning. The values following the pre-processing would be identical to those obtained by the above-described weighting according to the curve modification set forth in the example.

Figure 12:
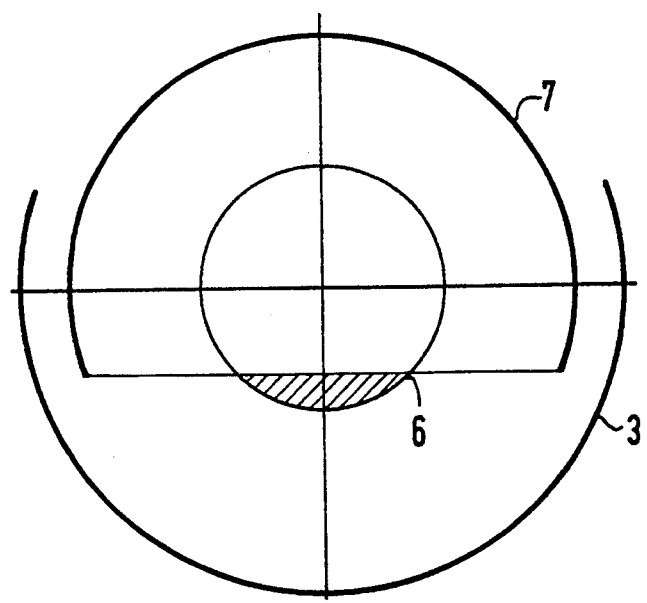
FIG. 12 is a simplified illustration of a sub-minimal computer tomography apparatus design, constructed in accordance with the principles of the present invention.

The method disclosed herein also can be employed for a sub-minimal device design, i.e., a device which does not exhibit the aforementioned property of minimal geometry. Such a sub-minimal device is schematically shown in FIG. 12. The shaded region can be reconstructed without disturbances in accordance with the present method, however, this region can be omitted in the image reconstructions since it is usually a diagnostically irrelevant region, such as the region beneath the patient support 10. Removal of this region from the reconstructed image is a standard technique in known image reconstruction methods, and such removal is referred to as a "bottom chop."

Figure 13:
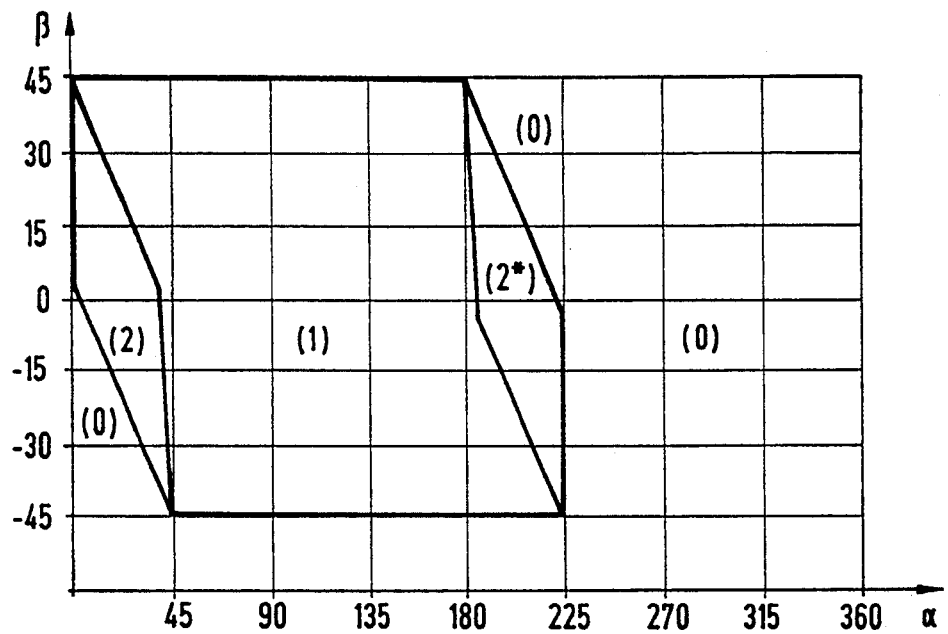
FIG. 13 illustrates a sinogram for minimal geometry initially obtained in an apparatus in accordance with FIG. 2.
Figure 14:
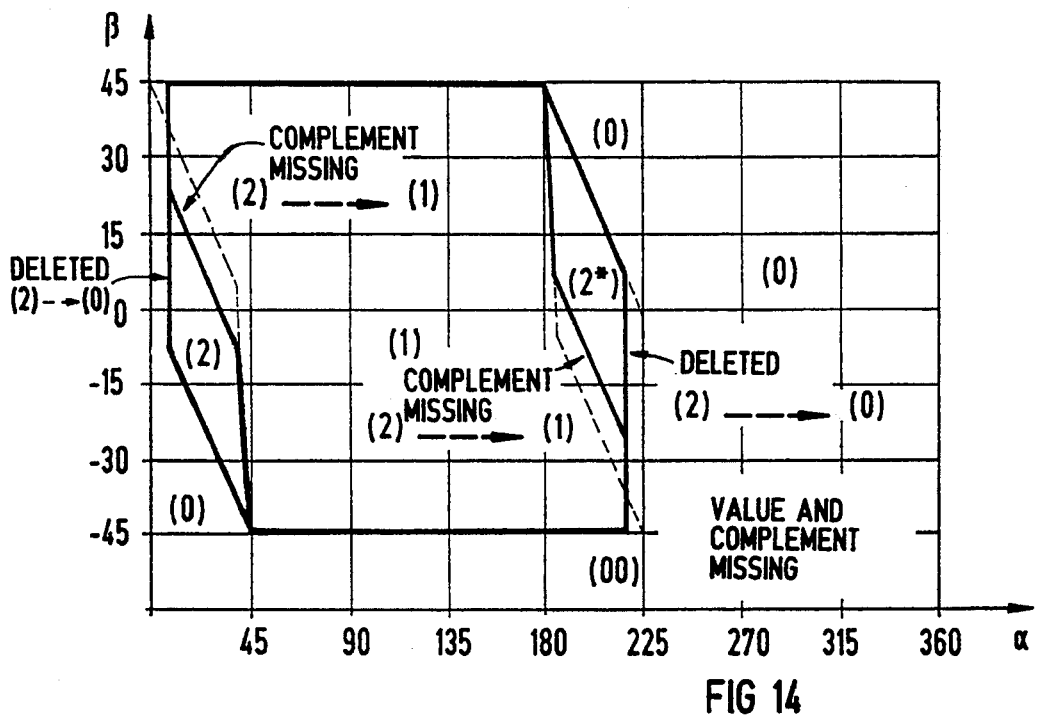
FIG. 14 illustrates a sinogram of sub-minimal geometry, obtained in accordance with FIG. 12.

A sinogram as initially obtained in a sub-minimal device of the type shown in FIG. 12 (before modification in accordance with the invention) is shown in FIG. 13 without a bottom chop, and FIG. 14 shows the same sinogram with a bottom chop.

In certain known image reconstruction methods, the measured data may be already weighted for other reasons, in which case the weighting in accordance with the present invention, to resolve the problems associated with the double partial ring geometry, can be combined with the other weighting, such as by modifying such known weightings. For example, only a portion of the measured data may be subjected to a separate treatment for correcting the problems associated with the double partial ring geometry, and data which would receive the constant weighting of 0 or 1 may be processed unmodified.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A computer tomography apparatus comprising:
   a partial ring x-ray means for generating a fan beam movable around an examination volume for irradiating said examination volume from different directions;
   a partial ring detector means disposed for receiving said fan beam after passing through said examination volume and for generating a data set of measured attenuation values for each transirradiated direction;
   means for generating a sinogram from said data sets having a plurality of data regions separated by boundaries respectively having sharp corners;
   means for generating weighted data by weighting data in said sinogram in said data regions with respectively different constant weighting factors and by weighting selected data at said boundaries for smoothing said boundaries to eliminate said sharp corners; and
   means for reconstructing an image from said weighted data using standard computer tomography image reconstruction techniques.

2. A method for operating a computer tomography apparatus comprising:
   transirradiating an examination volume from a plurality of different directions with an x-ray fan beam moving around said examination volume;
   detecting said fan beam after passing through said examination volume at each of said directions, and generating a data set of measured attenuation values for each of said directions;
   generating a sinogram from said data sets having a plurality of data regions separating by boundaries respectively having sharp corners;
   generating weighted data by weighting data in said sinogram in said data regions with respectively different constant weighting factors and by weighting selected data at said boundaries for smoothing said boundaries to eliminate said sharp corners; and
   reconstructing an image from said weighted data using standard computer tomography image reconstruction techniques.

3. A method as claimed in claim 2 comprising the additional step of weighting said data in said sinogram with a further weighting factor, and wherein the step of generating weighting data is further defined by generating said weighted data by modification of said further weighting factor.

4. A method as claimed in claim 3 wherein the step of generating weighted data by modification of said further weighting factor is further defined by generating weighted data by modifying said further weighting factor only for said selected data at said boundaries, and leaving said further weighting factor for a remainder of said data in said sinogram unmodified.

* * * * *